United States Patent [19]

Piraka

[11] Patent Number: 5,876,412
[45] Date of Patent: Mar. 2, 1999

[54] SURGICAL SUTURING DEVICE

[76] Inventor: Hadi A. Piraka, 21257 Woodfarm, Northville, Mich. 48167

[21] Appl. No.: 870,538

[22] Filed: Jun. 6, 1997

[51] Int. Cl.⁶ .................................................. A61B 17/04
[52] U.S. Cl. ........................... 606/144; 606/139; 606/147
[58] Field of Search ..................................... 606/139, 144, 606/146, 147, 148

[56] References Cited

U.S. PATENT DOCUMENTS

| | | | |
|---|---|---|---|
| 5,454,823 | 10/1995 | Richardson et al. | 606/148 |
| 5,480,406 | 1/1996 | Nolan et al. | 606/144 |
| 5,571,090 | 11/1996 | Sherts | 606/144 |
| 5,632,751 | 5/1997 | Piraka | 606/139 |

*Primary Examiner*—Gary Jackson
*Attorney, Agent, or Firm*—Alex Rhodes

[57] ABSTRACT

A surgical suturing device for repairing wounds and incisions. In a first aspect of the invention, a slender elongated rod is connected to a movable handle to bring together a pair of pivotally connected needle holders. The needle holders have a pair of phased latches which control wire-like retainers which move in and out of end portions of the pivotally connected needle holders. The wire-like retainers interlock with circular grooves in opposite thread and point end portions of a surgical needle. Each time the slender rod is advanced toward the needle holders, the needle holders pivot toward each other and the rod simultaneously contacts the latches to alternately hold and release the thread and end portions of the needle. In a second aspect of the invention, each time the slender rod is advanced toward the needle holders, resilient members on sides of the needle holders simultaneously depress to alternately hold and release the thread and point end portions of the needle.

11 Claims, 6 Drawing Sheets

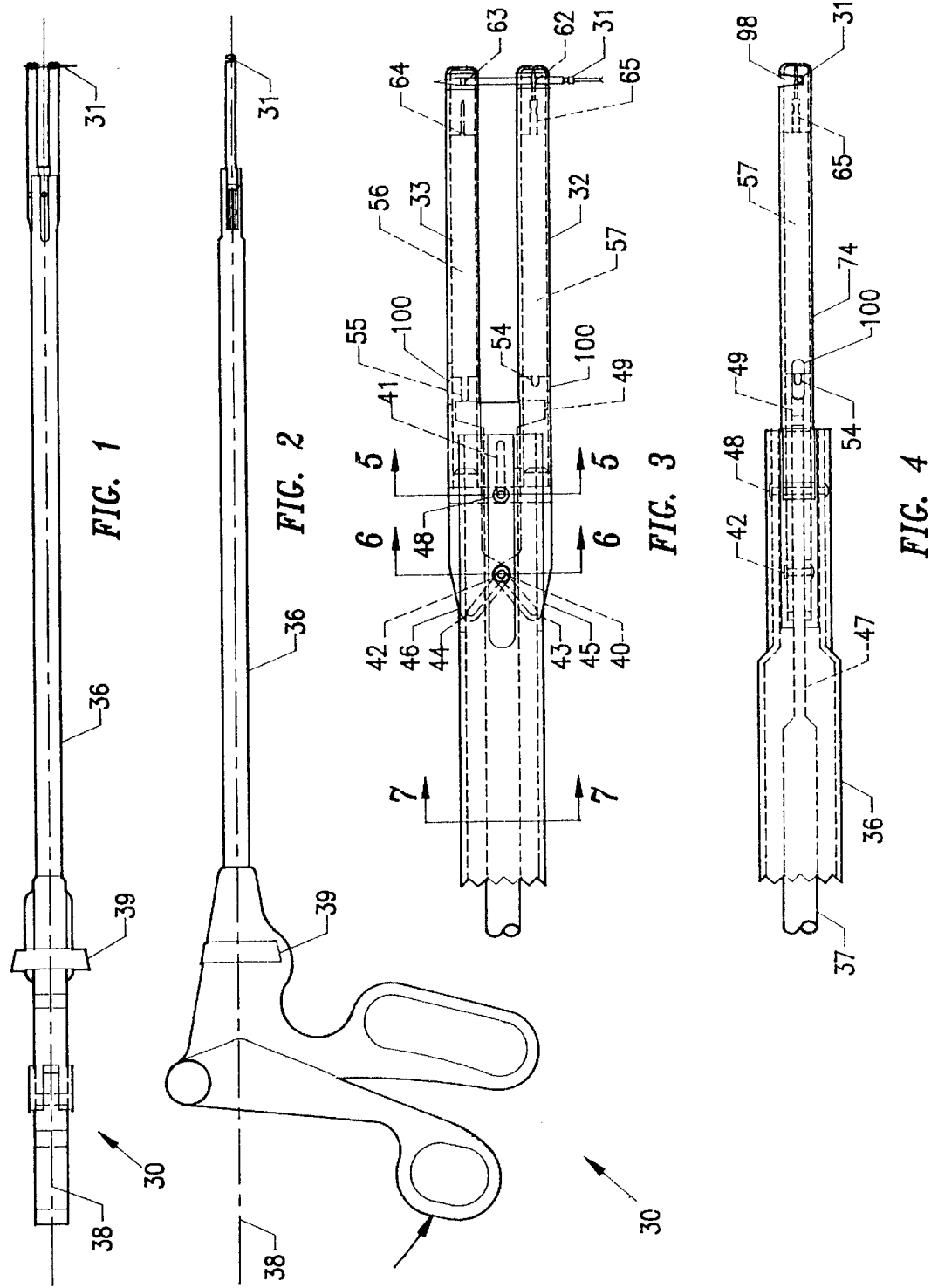

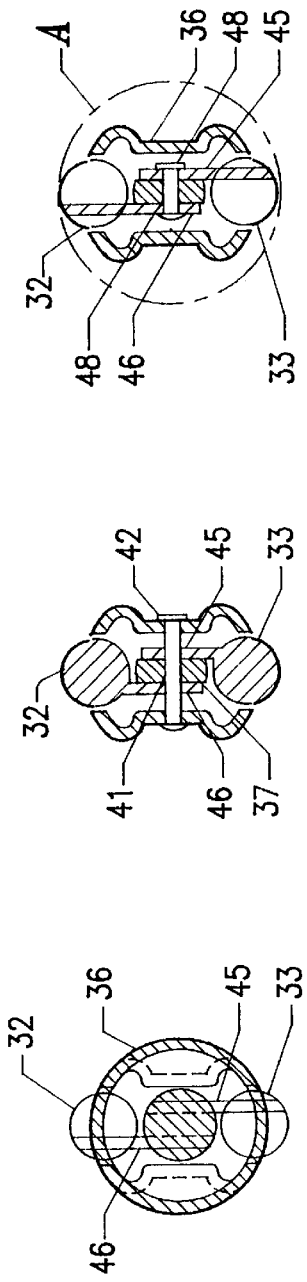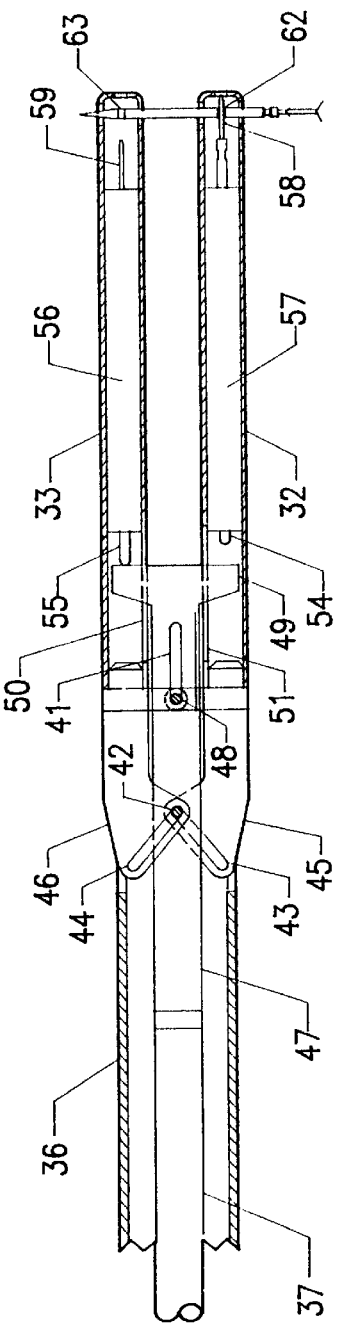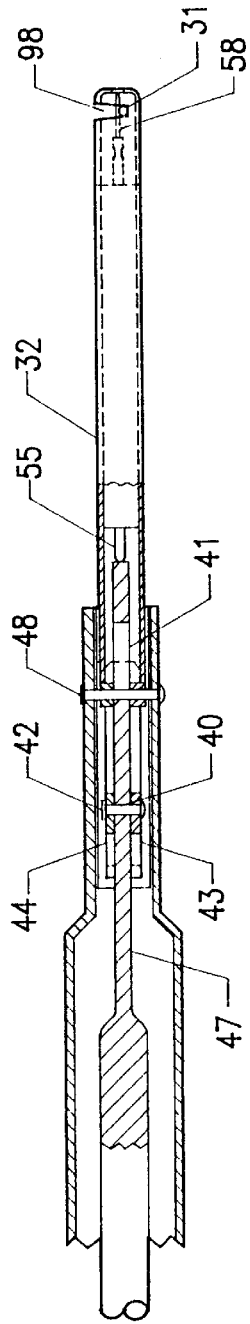

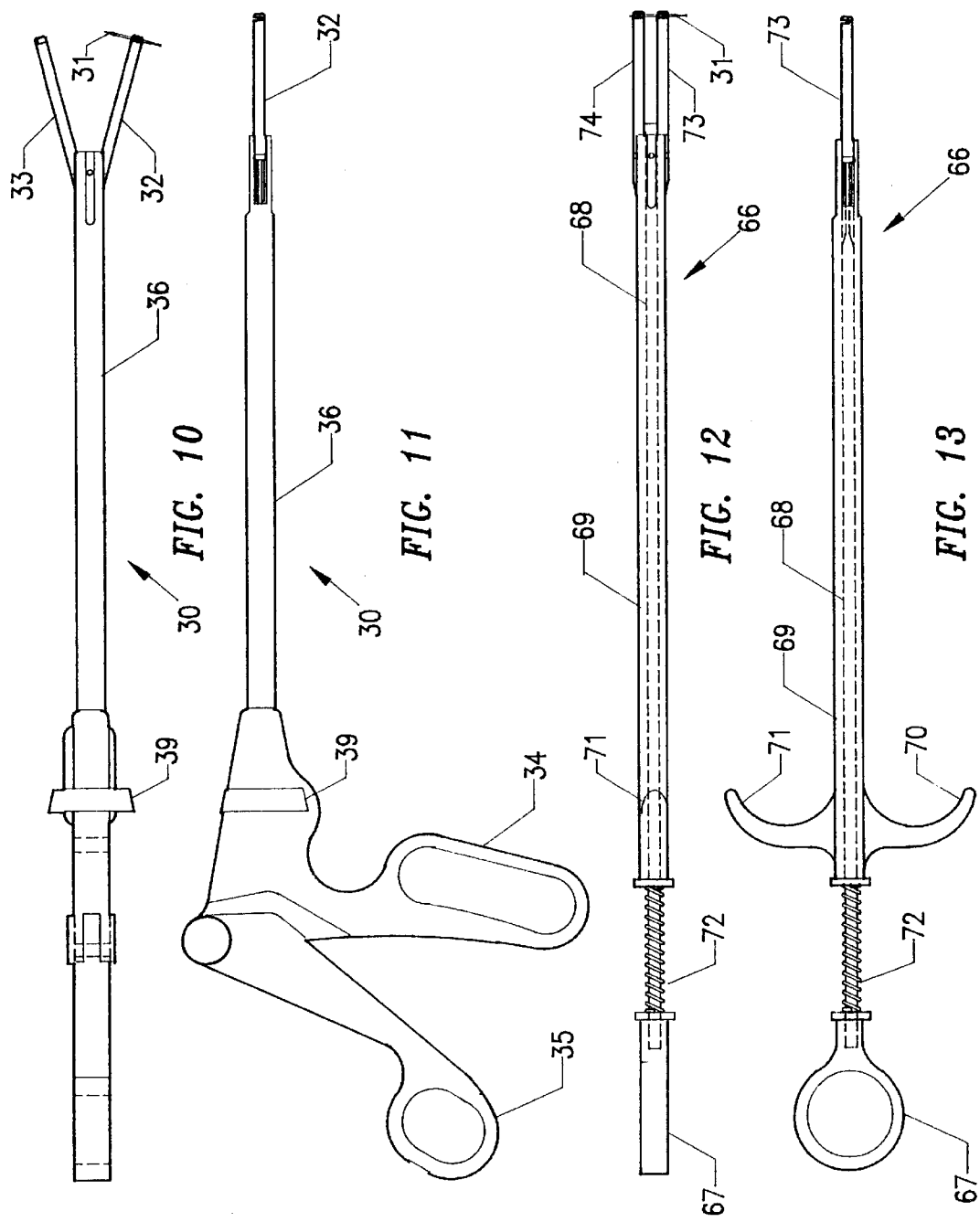

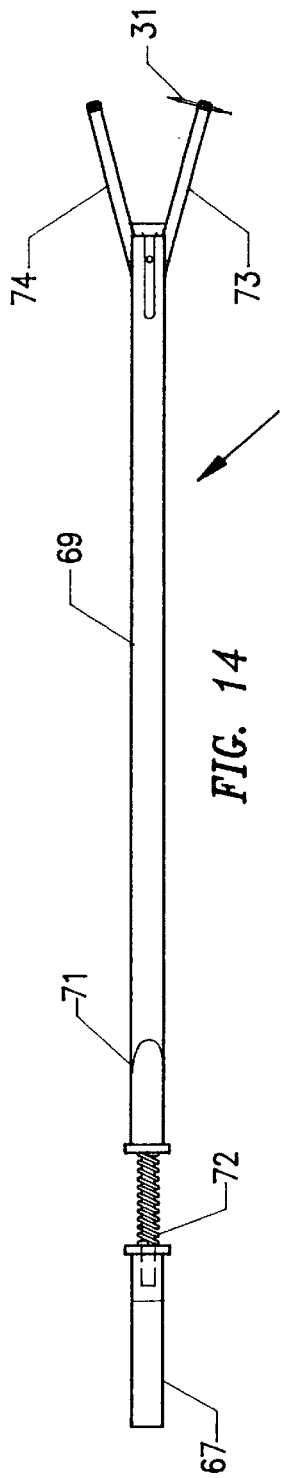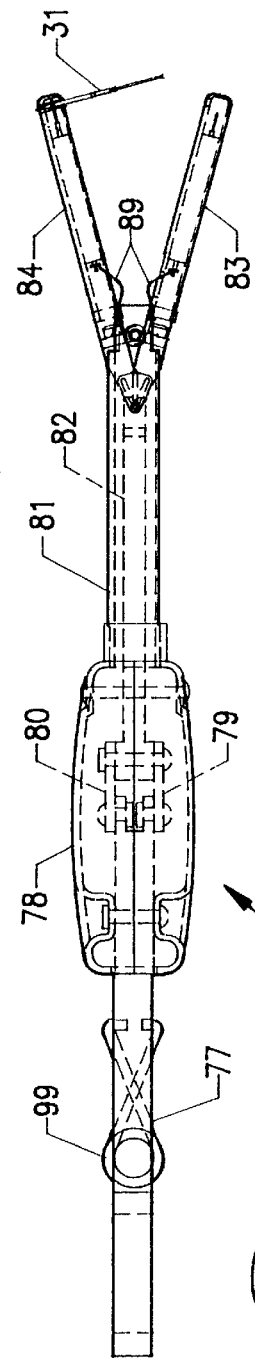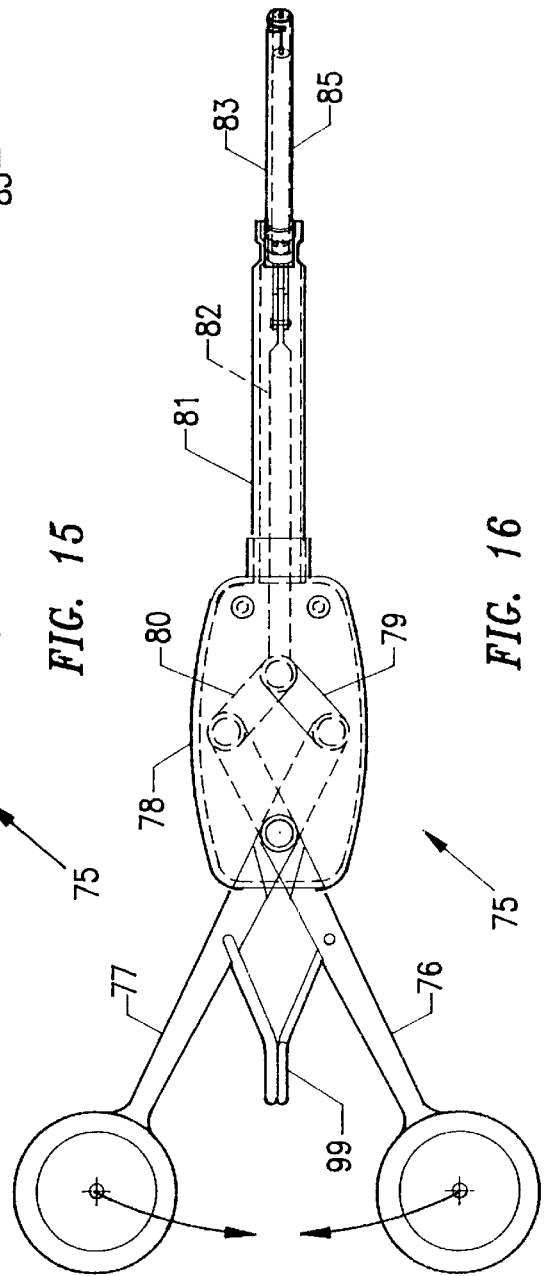

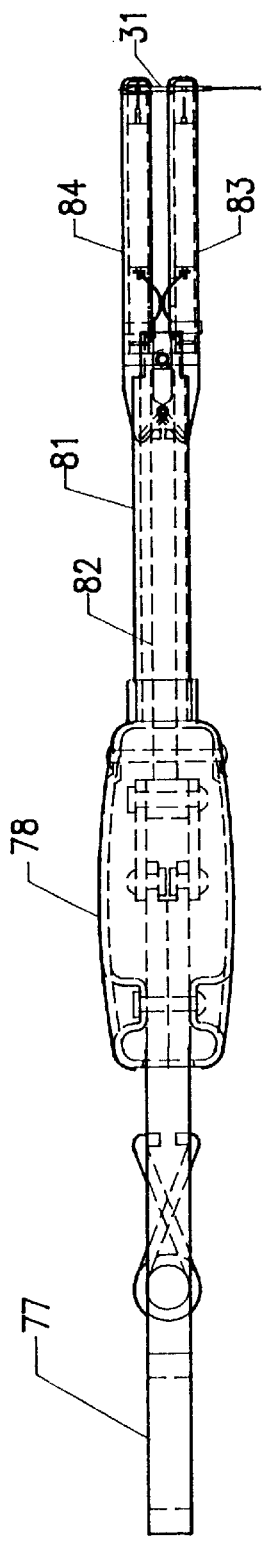
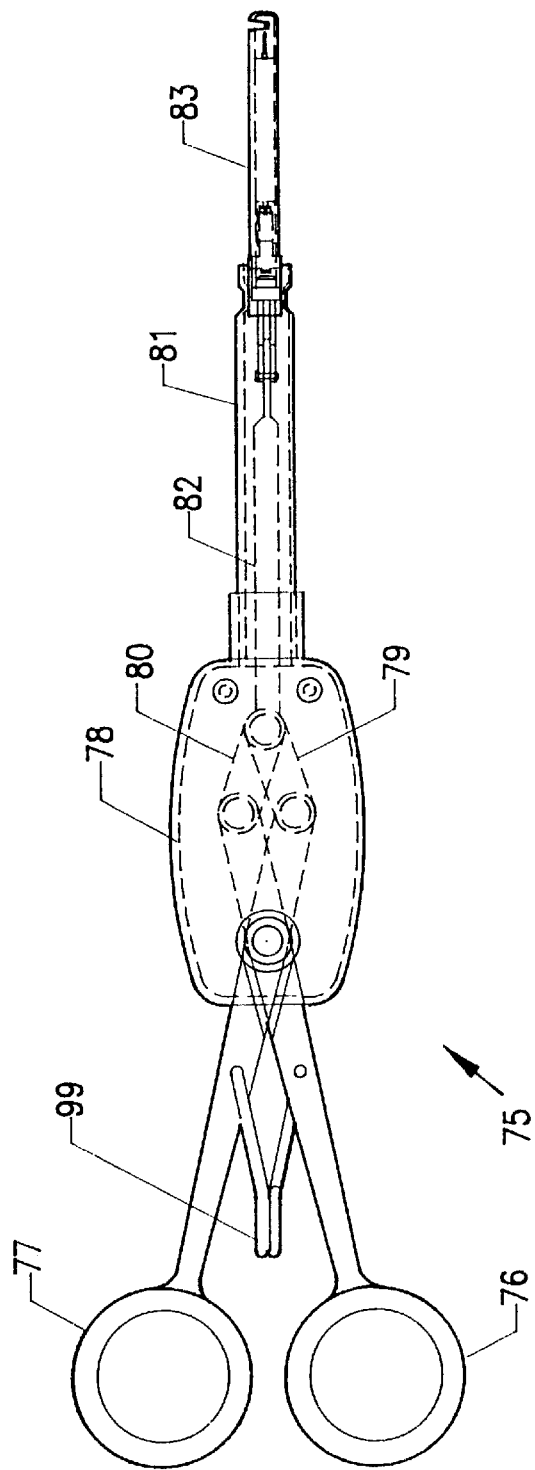
FIG. 17
FIG. 18

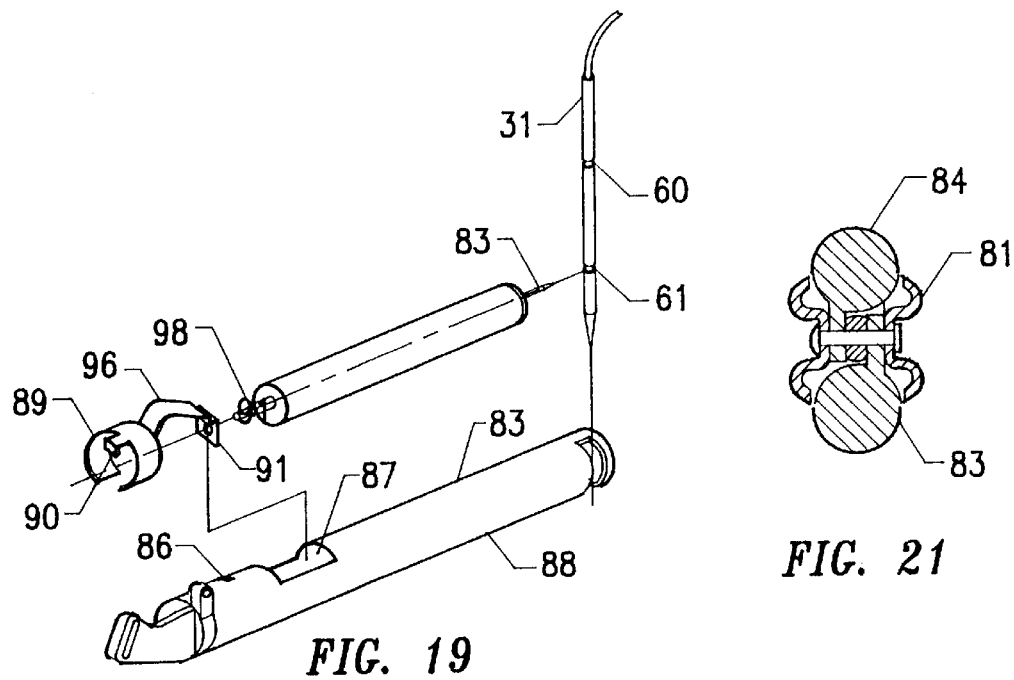
FIG. 19
FIG. 21
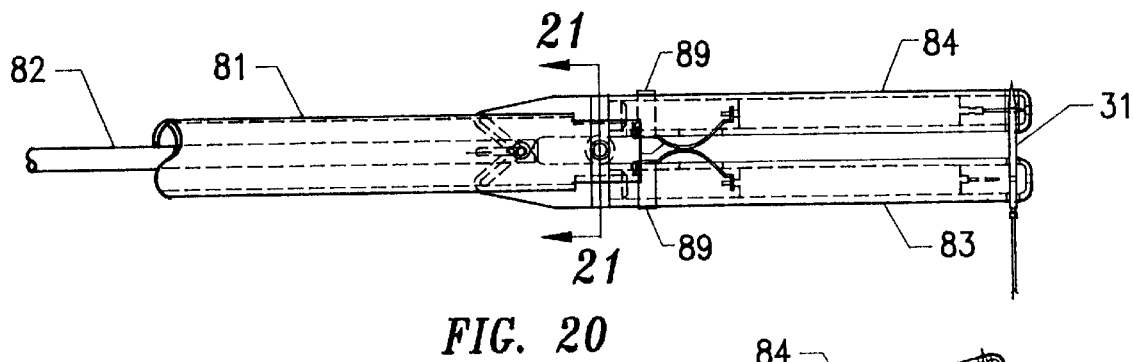
FIG. 20
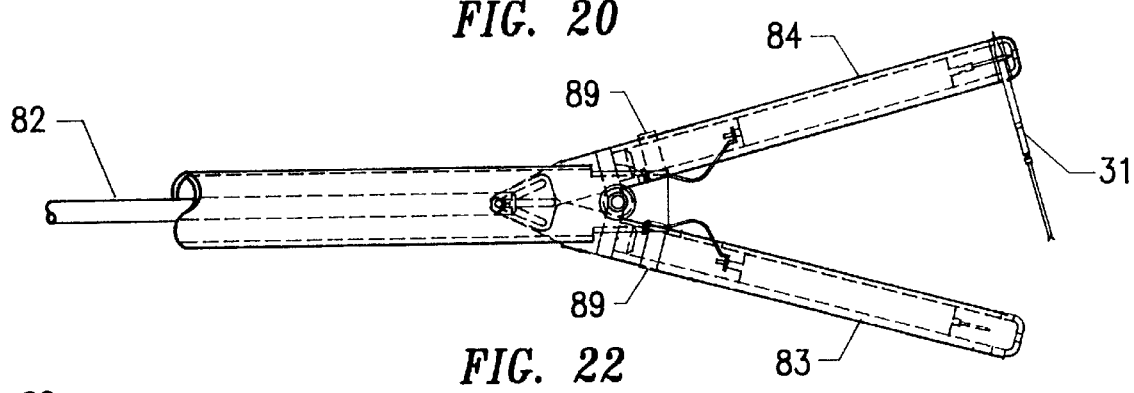
FIG. 22
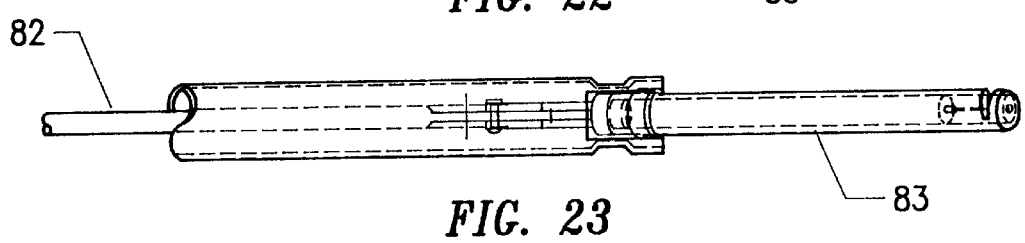
FIG. 23

SURGICAL SUTURING DEVICE

FIELD OF THE INVENTION

This invention relates to surgical devices and more particularly to a suturing device for repairing wounds and incisions.

BACKGROUND OF THE INVENTION

Suturing is a common surgical procedure for repairing wounds and incisions. During certain forms of surgery, in particular, endoscopic surgery, only small amounts of space are available for viewing surgical sites and repairing wounds and incisions. Viewing devices, such as telescopes and TV cameras reduce the space for making sutures and thus substantially increase the time for performing surgeries. Also, a surgeon's hands are sometimes punctured with needles, placing the surgeon at risk to serious and sometimes fatal infections.

In my U.S. patent application Ser. No. 08/508,669, an improved endoscopic suturing device was disclosed for repairing wounds and incisions. One distinguishing feature of the invention is that opposite ends of a needle are simultaneously grasped and released when a pair of pivotally connected needle holders are brought together by a surgeon. Another distinguishing feature of the invention is that only one hand is required during the grasping and releasing of the opposite ends of the needle, thus freeing the other hand for other tasks, such as manipulating a telescope.

Several important benefits are achieved with this device. One benefit is that the suturing device is particularly useful where only limited amounts of space are available for performing surgery, Another important benefit is that the time for performing surgery is reduced, thereby reducing stresses on patients and increasing the utilization of operating rooms. Another benefit is a reduced exposure of surgeons to infections from a needle puncture.

SUMMARY OF THE INVENTION

The present invention is a development of my invention which is disclosed in my U.S. patent application Ser. No. 08/508,669, which is incorporated herein by reference. The invention resides in features which individually and collectively combine to simultaneously hold and release the opposite ends of a needle.

In a first aspect of the present invention, a pair of needle holders have slender wire-like extensible members which alternately extend and retract out of end portions of a pair of pivotally connected needle holders. Each time the needle holders are brought together, one of the wire-like retaining members engages a circular groove in one end portion of a needle and the other wire-like retaining member disengages a circular groove in an opposite end portion of the needle. When this action is repeated, the movements of the wire-like retaining members are reversed. Thus the opposite end portions of the needle are alternately and simultaneously grasped and released.

In a second aspect of the invention, when the pair of elongated needle holders are brought together, a push rod initiates the simultaneous holding and releasing of opposite end portions of the needle.

In a third aspect of the invention, a pair of resilient members compress to initiate the simultaneous holding and releasing of the opposite end portions of the needle.

In third and fourth aspects of the invention, alternate means are disclosed for separating and pivoting the needle holders together.

Further benefits and features of the invention will become apparent from the ensuing description and drawings which further disclose the invention and the manner of using the invention. The property in which exclusive rights are claimed is set forth in each of the numbered claims at the conclusion of the detailed description.

BRIEF DESCRIPTION OF THE DRAWINGS

The invention will be better understood and further objects, characterizing features, details and advantages thereof will appear more clearly with reference to the diagrammatic drawings illustrating a presently preferred specific embodiment of the invention by way of non-limiting example only.

FIG. 1 is a top view of a suturing device and needle showing a pair of pivotally connected needle holders adjacent to each other.

FIG. 2 is a right side view of the suturing device.

FIG. 3 is an enlarged right side view of a pair of needle holders.

FIG. 4 is an enlarged top view of the pair of needle holders.

FIG. 5 is an enlarged cross-sectional view taken on the line 5—5 in FIG. 3.

FIG. 6 is an enlarged cross-sectional view taken on the line 6—6 in FIG. 4.

FIG. 7 is an enlarged cross-sectional view taken on the line 7—7 in FIG. 4.

FIG. 8 is an enlarged top view of the pair of needle holders shown in partial cross-section.

FIG. 9 is an enlarged right side view of the pair of needle holders shown in partial cross-section.

FIG. 10 is a top view of the suturing device with the pair of needle holders separated from each other.

FIG. 11 is a right side view of the suturing device and needle showing the pair of pivotally connected needle holders separated from each other.

FIG. 12 is a top view of a second embodiment of the suturing device.

FIG. 13 is a right side view of the second embodiment showing the pair of needle holders adjacent to each other.

FIG. 14 is a right side view of the second embodiment showing the pair of needle holders separated from each other.

FIG. 15 is a top view of a third embodiment of the suturing device showing the pair of needle holders separated from each other.

FIG. 16 is a right side view of FIG. 15.

FIG. 17 is a top view of a third embodiment of the suturing device showing the pair of needle holders adjacent to each other.

FIG. 18 is a right side view of FIG. 17.

FIG. 19 is an enlarged exploded view of a portion of one of the needle holders of the third embodiment.

FIG. 20 is an enlarged partial view of FIG. 17.

FIG. 21 is an enlarged cross-sectional view taken on the line 21—21 in FIG. 20.

FIG. 22 is an enlarged partial view of FIG. 15.

FIG. 23 is an enlarged partial view of FIG. 16.

DETAILED DESCRIPTION OF THE PREFERRED EMBODIMENT

Referring now to the drawings wherein like numerals designate like and corresponding parts throughout the several views, in FIGS. 1 through 21, inclusive, a first embodiment is shown of an improved surgical suturing device 30 for endoscopic and general surgery. The suturing device 30 is a development of the suturing device which is disclosed in my U.S. patent application Ser. No. 08/508,669, incorporated herein by reference.

A characteristic feature of my suturing device 30 is that opposite end portions of a needle 31 are interlocked with distal end portions of a pair of pivotally connected needle holders 32, 33 to simultaneously hold and release the opposite end portions of the needle 31 as shown in FIG. 1. Another characteristic feature is that only a single hand is used for simultaneously holding and releasing the opposite end portions of the needle 31.

The suturing device 30 in FIGS. 1 through 11 is particularly adapted for endoscopic surgical procedures but can be used for general surgical procedures. For endoscopic surgical procedures, the needle holders 32, 33 are preferably of such small size that they can be passed through a 10 mm cannula represented by circle "A" shown in FIG. 5. The suturing device 30 broadly comprises a pair of pivotally connected handles 34, 35, a push rod 37 connected at one end portion to one of the handles 34, 35, and the pair of pivotally connected needle holders 32, 33. One of the handles 34 is fixed and is attached to an end portion of an outer tube 36 which encloses the slender elongated push rod 37. The other handle 35 is movable and is pivotally attached to the fixed handle 34 above the push rod 37. When the handles 34, 35 are pivoted together as shown in FIG. 1, the push rod 37 advances toward the needle holders 32, 33 to bring the needle holders 32, 33 together.

The outer tube 36, push rod 37 and needle holders 32, 33 are preferably rotatable in the fixed handle 34, in the usual manner, about a longitudinal axis 38 to assist a surgeon in suturing an incision and viewing a surgical site. The outer tube 36, push rod 37 and needle holders 32, 33 are rotated in the fixed handle 34 by means of a small wheel 39 which is rotatable in the fixed handle 34.

Referring to FIGS. 3 through 9, one end portion 47 of the push rod 37 is blade shaped and has a hole 40 and an elongated slot 41. A pin 42 extends through the hole 40 of the push rod 37 and engages a pair of angular slots 43, 44 in brackets 45, 46 which are attached to end portions of the needle holders 32, 33. The brackets 45, 46 straddle the blade shaped end portion 47 of the push rod 37 as shown in FIG. 5. The needle holders 32, 33 are pivotally connected to an end portion of the outer tube 36 by means of a second pin 48 which extends through the slot 41 of the push rod 37 and outer tube 36 as shown in FIG. 6. When the movable 35 and fixed 34 handles are brought together, the first pin 42 advances in the angular slots 43, 44 to rotate the needle holders 32, 33 about the second pin 48 and bring the needle holders 32, 33 together as shown in FIG. 1. When the movable 35 and fixed 34 handles are separated, the push rod 37 and first pin 42 move in the angular slots 43, 44 away from the needle holders 32, 33 to rotate the needle holders 32, 33 about the second pin 45 and separate the needle holders 32, 33 as shown in FIG. 10.

Referring now to FIG. 8, an enlarged distal end portion 49 of the push rod 37 extends laterally through slots 50, 51 in opposite sides of outer tubes 52, 53 of the needle holders 32, 33. The enlarged end portion 49 of the push rod 37 is aligned with axial plungers 54, 55 which project out of inner tubes 56, 57 of the needle holders 32, 33.

When the needle holders 32, 33 are brought together as shown in FIG. 1, the enlarged end portion 49 of the push rod 37 depresses the plungers 54, 55 to operate latches inside of the needle holders 32, 33 and cause wire-like retainers 58, 59 to extend and retract out of end portions of inner tubes 56, 57 of the needle holders 32, 33. The wire-like retainers 58, 59 simultaneously interlock and disengage with circular grooves 62, 63 in thread 60 and point 61 end portions of the needle 31. With reference to FIG. 9, the outer tubes 52, 53 of the needle holders 32, 33 have "V-notches" to allow the ends of the needle 31 to enter the needle holders 32, 33. Typical latches (not shown) inside of the inner tubes 56, 57 retain and release the needle retaining members 58, 59 are disclosed in my application which is incorporated herein by reference.

The construction and operation of the needle holders 32, 33 is also more fully disclosed in the patent application which is incorporated herein by reference. The operation of the needle holders 32, 33 is similar to a pair of out of phase ball point pens of the type wherein slender cartridges are alternately extended and retracted by simultaneously depressing plungers which extend out of end portions of the pens. When the plungers are simultaneously depressed, a latch in one of the pens engages to retain a cartridge in an extended position while a latch in the other pen disengages to retract a cartridge in the other pen by a spring. In the present invention, the wire-like needle retaining members 58, 59 are attached to slender shafts 64, 65 in lieu of the cartridges.

Openings 100 are provided in the outer tubes 52, 53 for phasing the latches of the needle holders 32, 33. With reference to FIG. 3, it will be observed that when one of the wire-like retaining members 58 is engaged with the circular groove 62 at the thread end portion of the needle 31, the other of the wire-like retaining members 59 is not engaged with the circular groove 63 at the pointed end portion of the needle 31.

Referring now to FIGS. 12 through 14, a second embodiment 66 is disclosed which is generally comprised of a loop-shaped handle 67 attached to a push rod 68 which is slidably mounted in a slender tube 69. At one end portion of the tube 69 there is a pair of laterally extending arcuate arms 70, 71 which cooperate with the loop-shaped handle 67 to selectively move the push rod 68 in the tube 69. Surrounding an exposed end portion of the push rod 68, adjacent to the loop-shaped handle 67, is a coil spring 72 which assists in retracting the push rod 68 into the tube 69. At the opposite end portion of the tube 69 are the pair of needle holders 73, 74 as hereinbefore described. The pair of needle holders 73, 74 are attached to the push rod 68 and operate in the same manner as the earlier described embodiment 30.

In FIGS. 15 through 23, a third embodiment 75 is illustrated for repairing wounds and incisions which are readily accessible and wounds and incisions which require higher forces for penetrating tissue. The third embodiment 75 also includes an alternate means for latching and unlatching the needle holders which is also adaptable to the earlier disclosed embodiments 30, 66. The third embodiment 75 broadly comprises a pair of crossed handles 76, 77, pivotally mounted in a housing 78, an assist spring 99 for separating the handles 76, 77, a pair of links 79, 80, a slender tube 81, a push rod 82 and a pair of needle holders 83, 84. The links 79, 80 are pivotally connected at end portions and to the push rod 82. Opposite end portions of the links 79, 80 are pivotally connected to end portions of the crossed handles 76, 77. The needle holders 83, 84 are similar to the previously described needle holders 32, 33 except for a novel means of depressing the plungers 54, 55.

The means for depressing the plungers 54, 55 can be understood by reference to FIGS. 19 through 23, inclusive.

In each of the needle holders 83, 84 there is a pair of openings 86, 87 in an outer tube 88 for mounting a leaf spring 89 to an outer tube 88. At one end portion of the spring 89 there is a tab 90 which engages one of the openings 86 to axially and radially locate the spring 89 on the outer tube 88. At the opposite end portion of the spring 89 there is a second tab 91 with an aperture 92. The second tab 91 extends through the second opening 87 to engage a shoulder 93 of a plunger 94 of the needle holders 83, 84. Between the tabs 90, 91 of the spring 89 is an outward projecting loop-shaped portion 96. When the needle holders 83, 84 are brought together as shown in FIG. 20, the loop-shaped portions 96, 97 of the springs 89 deflect to depress the plungers 94, 95, thereby engaging a latch of one needle holder and disengaging the other latch.

From the foregoing it will be apparent that the present invention provides improvements and significant benefits for repairing wounds and incisions during endoscopic surgical procedures as well as other surgical procedures where wounds and incisions are readily accessible.

Although only several embodiments have been illustrated and described, it is not my intention to limit the scope of my invention to these embodiments, since other embodiments can be developed by changes in material and shape as well as substitution and arrangements of parts without departing from the spirit thereof.

I claim:

1. In a surgical suturing device of the type wherein opposite thread and point end portions of a surgical needle are simultaneously held and released by said surgical device, the improvement comprised of: a means for simultaneously holding and releasing said opposite end portions of said surgical needle, said means comprising: a circular groove in at least one of said needle's end portions; a pair of pivotally connected needle holders, one of said needle holders having an extensible wire-like distal end portion for holding one of said needle's end portions by interlocking said wire-like portion with said circular groove; and a pair of latches for simultaneously interlocking said wire-like end portion of said needle holder with said circular groove and releasing said other end portion of said needle.

2. The improvement as recited in claim 1 further comprising a means for simultaneously engaging one of said latches and disengaging the other of said latches.

3. The improvement as set forth in claim 2 wherein said means for simultaneously engaging one of said latches and disengaging the other of said latches comprises: an axially movable rigid member for simultaneously operating each of said latches.

4. The improvement as recited in claim 3 wherein said means for simultaneously engaging one of said latches and disengaging the other of said latches comprises: a slender tube, said tube having a pair of laterally extending arms; a slender elongated rod slidably mounted in said tube, said rod having a loop end portion extending outwardly from said laterally extending arms portion of said tube and an opposite end portion for simultaneously operating each of said latches.

5. The improvement as set forth in claim 2 wherein said means for simultaneously engaging one of said latches and disengaging the other of said latches comprises: a resilient member mounted on each of said needle holders for simultaneously engaging one of said latches and releasing the other of said latches when said needle holders are brought adjacent to each other.

6. The improvement as recited in claim 2 wherein said means for simultaneously engaging one of said latches and disengaging the other of said latches comprises: a pair of pivotally connected handles, said handles including a fixed handle and a movable handle; a slidably mounted elongated slender rod pivotally connected to said movable handle, said slender rod having an enlarged end portion for simultaneously depressing a pair of members extending out of said latches.

7. The improvement as recited in claim 2 wherein said means for simultaneously engaging one of said latches and disengaging the other of said latches comprises: a pair of pivotally connected handles; a pair of links, each of said links having an end portion pivotally connected to an end portion of said other link and an opposite end portion pivotally connected to a distal end portion of one of said handles; a slidably mounted rod, said rod having an end pivotally connected to said pivotally connected end portions of said links and an opposite end portion for simultaneously operating each of said latches.

8. In a surgical suturing device of the type wherein opposite ends of a needle are simultaneously held and released by said surgical device, the improvement comprised of: a surgical needle, said needle having a thread end portion, a point end portion, and a circular groove in said thread end and said point end portions; a pair of pivotally connected handles, said handles including a fixed handle and a movable handle; a slidably mounted elongated slender rod for fore and aft movement toward and away from said surgical needle and pivotally connected at an end portion thereof to said movable handle, said slender rod having an enlarged opposite end portion for simultaneously operating a latch of each of a pair of needle holders to alternately engage and disengage a wire-like member slidably mounted in each of said needle holders with one of said needle's circular grooves; and a pair of pivotally connected needle holders for simultaneously holding and releasing said thread and point end portions of said surgical needle, each of said needle holders having a latch and a slidably mounted wire-like member for alternately interlocking said needle holders with one of said circular grooves to hold and release said thread and said point end portions of said needle.

9. In a surgical suturing device of the type wherein opposite ends of a needle are simultaneously held and released by said surgical device, the improvement comprised of: a surgical needle having a thread end portion, a point end portion, and a circular groove in said thread end and in said point end portions; a pair of pivotally connected handles; a pair of links, each of said links having an end portion pivotally connected to an end portion of said other link and an opposite end portion pivotally connected to a distal end portion of one of said handles; a slidably mounted rod, said rod having an end portion pivotally connected to said pivotally connected end portions of said links, said rod having an enlarged end portion for simultaneously operating a latch in each of a pair of needle holders to alternately engage and disengage a wire-like member of each of said needle holders with one of said needle's circular grooves; and a pair of pivotally connected needle holders for simultaneously holding and releasing said opposite end portions of said surgical needle, each of said needle holders having a latch and a wire-like member for alternately interlocking with one of said circular grooves to hold and release said thread and said point end portions of said needle.

10. A surgical suturing device for repairing wounds and incisions, comprised of: a surgical needle, said needle having a thread end portion, a point end portion, and a circular groove at said thread and said point portions; a pair of pivotally connected handles, said handles including a fixed handle and a movable handle; a slidably mounted elongated slender rod pivotally connected to said movable handle, a pair of pivotally connected needle holders, each of said needle holders having an angular slot at an end portion of said slender rod, a slidably mounted wire-like member for engaging one of said circular grooves of said needle, and a latch to alternately hold and release one of said needle's end portions; and a means for simultaneously engaging one of said latches and releasing the other of said latches; said means comprising: an enlarged end portion of said slidably mounted rod for simultaneously operating each of said latches.

11. The surgical suturing device as recited in claim 10 wherein said means for simultaneously engaging one of said latches and releasing the other of said latches is comprised of a resilient member in each of said latches for simultaneously operating said latches when said needle holders are brought together to depress both of said resilient members.

* * * * *

UNITED STATES PATENT AND TRADEMARK OFFICE
CERTIFICATE OF CORRECTION

PATENT NO. : 5,876,412
DATED : March 2, 1999
INVENTOR(S) : Hadi A. Piraka

It is certified that error appears in the above-identified patent and that said Letters Patent is hereby corrected as shown below:

Column 3, line 58, after pin; change "45" to --48--

Column 4, line 46, after "73" insert --74--

Signed and Sealed this

Thirteenth Day of July, 1999

Attest:

Q. TODD DICKINSON

Attesting Officer

Acting Commissioner of Patents and Trademarks